(12) United States Patent
Schmid

(10) Patent No.: US 8,062,648 B2
(45) Date of Patent: Nov. 22, 2011

(54) **FORMULATIONS CONTAINING MELATONIN, *GINKGO BILOBA*, AND BIOTIN**

(75) Inventor: Hans W. Schmid, Zug (CH)

(73) Assignee: ASAT AG Applied Science & Technology, Zug (CH)

(*) Notice: Subject to any disclaimer, the term of this patent is extended or adjusted under 35 U.S.C. 154(b) by 1735 days.

(21) Appl. No.: 10/533,516

(22) PCT Filed: Oct. 30, 2003

(86) PCT No.: PCT/EP03/12097
§ 371 (c)(1),
(2), (4) Date: Sep. 21, 2005

(87) PCT Pub. No.: WO2004/039454
PCT Pub. Date: May 13, 2004

(65) Prior Publication Data
US 2006/0099278 A1    May 11, 2006

Related U.S. Application Data

(63) Continuation-in-part of application No. 10/353,056, filed on Jan. 29, 2003, now abandoned.

(30) Foreign Application Priority Data

Oct. 30, 2002  (DE) .................................. 102 50 646
Nov. 18, 2002  (DE) .................................. 202 17 814

(51) Int. Cl.
*A61K 8/02* (2006.01)
*A61K 8/18* (2006.01)

(52) U.S. Cl. ........................ 424/401; 424/752; 514/880

(58) Field of Classification Search ........................ None
See application file for complete search history.

(56) References Cited

U.S. PATENT DOCUMENTS

| | | | |
|---|---|---|---|
| 4,654,361 A | 3/1987 | Samples | |
| 4,746,674 A * | 5/1988 | Pierpaoli et al. | 514/415 |
| 4,818,540 A | 4/1989 | Chien et al. | |
| 5,006,004 A | 4/1991 | Dirksing | |
| 5,577,636 A | 11/1996 | Fukuoka | |
| 5,637,606 A * | 6/1997 | Matsumoto | 514/389 |
| 5,656,264 A * | 8/1997 | Hanada et al. | 424/70.1 |
| 5,750,107 A | 5/1998 | Nomura | |
| 5,952,373 A | 9/1999 | Lanzendörfer et al. | |
| 5,985,293 A | 11/1999 | Tachon et al. | |
| 6,007,834 A | 12/1999 | Merkus | |
| 6,013,279 A | 1/2000 | Klett-Loch | |
| 6,030,948 A | 2/2000 | Mann | |
| 6,281,241 B1 | 8/2001 | Elsner | |
| 6,524,619 B2 * | 2/2003 | Pearson et al. | 424/472 |
| 2001/0031744 A1 | 10/2001 | Kosbab | |
| 2002/0028257 A1 | 3/2002 | Catalfo et al. | |
| 2002/0034485 A1 * | 3/2002 | Noser et al. | 424/70.1 |
| 2002/0061870 A1 | 5/2002 | Pearson et al. | |
| 2002/0098253 A1 | 7/2002 | Riley | |
| 2002/0182196 A1 | 12/2002 | McCleary | |
| 2005/0271692 A1 | 12/2005 | Gervasio-Nugent | |

FOREIGN PATENT DOCUMENTS

| | | |
|---|---|---|
| AT | 367634 | 7/1982 |
| CN | 2223996 Y | 4/1996 |
| DE | 200 19 365 U1 | 2/2001 |
| DE | 10110418 A1 | 9/2002 |
| EP | 0 150 751 | 8/1985 |
| EP | 0867181 A1 | 9/1998 |
| GB | 2079238 A | 1/1982 |
| GB | 2 370 504 A | 7/2002 |
| JP | 410287531 A * | 10/1998 |
| WO | 02069927 A1 | 9/2002 |
| WO | WO 03/049687 A | 6/2003 |

OTHER PUBLICATIONS

Kljonowa et al., "Insecticidal and Miticidal Preparations for Treating Animals", 2001, pp. 184-185 Weterinarnyie preparaty w Rossii, Sprawotschnik, Moskau, Selkhozizat with translation.
Database WPI, Section Ch, Week, 199134, Derwent Publications Ltd., Class B01, AN 1991-248680 & JP 03 161426 A (Kobayash Kose KK) Jul. 11, 1991.
Kobayashi et al., "Effect of Leaves of Gingko Biloba on Hair Regrowth in C3H Strain Mice", Pharmaceutical Society of Japan. Journal—Yakugaku Zasshi, Pharmaceutical Society of Japan, vol. 113, No. 10, Oct. 1, 1993, pp. 718-724.

* cited by examiner

*Primary Examiner* — Robert A Wax
*Assistant Examiner* — Melissa Mercier
(74) *Attorney, Agent, or Firm* — Rothwell, Figg, Ernst & Manbeck, P.C.

(57) ABSTRACT

The present invention relates to a composition which comprises as active ingredients a combination of melatonin, *ginkgo biloba* and biotin. The composition is particularly suitable for producing formulations for topical application in the hair.

9 Claims, No Drawings

FORMULATIONS CONTAINING MELATONIN, *GINKGO BILOBA*, AND BIOTIN

CROSS REFERENCE TO RELATED APPLICATION

This application is a 35 USC §371 National Phase Entry Application from PCT/EP03/012097, filed Oct. 30, 2003, designating the United States, which is a continuation-in-part of U.S. Ser. No. 10/353,056 filed Jan. 29, 2003.

The present invention relates to a composition which comprises as active ingredients a combination of melatonin, *ginkgo biloba* and biotin. The composition is particularly suitable for producing formulations for topical application in the hair.

The use of melatonin for beneficially influencing hair growth is known. Melatonin has a stimulating effect on hair growth due to the selective interaction with proliferating cells of the hair follicles which control the growth of hair. This stimulating effect can be observed with the use of different concentrations of melatonin.

U.S. Pat. No. 5,952,373 describes a method for the treatment of skin, in which a composition which comprises as active ingredient one or more flavonoids is applied. There is no reference to the use of melatonin as active ingredient for improving hair growth.

US patent application US 2002/0061870 discloses a composition for the amelioration of hearing loss or tinnitus. This composition, which is administered in form of a tablet, comprises a large number of active ingredients, optionally also including melatonin, biotin or *ginkgo biloba*. There is no reference to the use for improving hair growth or to topical application.

It has surprisingly been found in the investigations leading to the present invention that the addition of *ginkgo biloba* and biotin in simultaneous use of melatonin enhance the effect of melatonin, and retention of melatonin on the surface of the scalp is increased.

One aspect of the present invention is thus a composition which comprises as active ingredients (a) melatonin or a derivative thereof, (b) *ginkgo biloba* as extract or/and one or more constituents thereof and (c) biotin. The composition is preferably a topical formulation suitable for pharmaceutical or/and cosmetic uses, in particular for application to the scalp.

The composition of the invention comprises a combination of active ingredients. The first component of this combination is melatonin or a melatonin derivative. Melatonin derivatives are preferably selected from 5-methoxytryptamine, 5-methoxytryptophan, 5-methoxytryptophol, 5-methoxyindole-3-acetic acid and 6-hydroxymelatonin. Besides these substances it is also possible to employ physiologically acceptable salts, esters and complex compounds thereof.

The second component of the composition is *ginkgo biloba*. *Ginkgo biloba* has a beneficial influence on various metabolic functions. A further advantageous property of ginkgo is the enhancement of the potential for trapping free radicals. A *ginkgo biloba* is preferably used as extract, in particular as dry extract, or/and one or more constituents thereof. Dry extracts from ginkgo leaves are particularly suitable for use of the composition of the invention.

A further component of the composition of the invention is biotin. Biotin displays its effect for example as coenzyme in fatty acid and amino acid metabolism, e.g. in transcarboxylation reactions.

The concentration of the active ingredients in the composition can be varied within wide limits—depending on the use. It is beneficial for the concentrations of the active ingredients each to be independently in the range between 0.0001% (weight) to 1% (weight) based on the total weight of the composition. The concentration of melatonin or a melatonin derivative is preferably 0.001% (weight) to 0.01% (weight). The concentration of *ginkgo biloba* is preferably 0.01% (weight) to 0.1% (weight). The concentration of biotin is preferably 0.002% (weight) to 0.05% (weight).

Preferably about 0.001 mg to about 10 mg, preferably about 0.01 mg to about 1 mg, of melatonin or melatonin derivative are administered per application.

The three active ingredient components of the composition of the invention display a profile of effects which promotes hair growth, provides protection from aging, improves hair thickness or/and reduces the telogen rate. The effect of melatonin on the hair follicle is surprisingly enhanced by the combination with *ginkgo biloba* and biotin. It is thus possible to employ even very low concentrations of melatonin, for example about 0.001-10 mg, preferably about 0.01-1 mg per application, with a satisfactory effect.

The combination of melatonin, *ginkgo biloba* and biotin can be administered in a suitable carrier system. The active ingredients are preferably present as solution or/and dispersion in a liquid, semisolid or solid carrier system. Examples of suitable carrier systems are liquids such as water or aqueous buffer solutions, physiologically tolerated organic solvents such as ethanol or combinations thereof, oil-water emulsions, water-oil emulsions, fats, polyethylene glycols, propylene glycols, glycerol, emulsifiers or combinations thereof, and other carriers or excipients used in pharmaceutical and cosmetic formulations.

The use of an aqueous carrier system, i.e. a carrier system with a water content of 50% (weight) or more, in particular of 60% (weight) or more, is preferred. The pH of an aqueous carrier system is preferably adjusted in a range between pH 3 and pH 6, particularly preferably in the range from pH 3.5 and pH 4.

These carrier systems advantageously enable targeted delivery of the active ingredients to the hair follicle. The placement of the active ingredients in the hair follicle is optimized thereby. Controlled absorption of the melatonin, *ginkgo biloba* and biotin active ingredients can moreover be made possible by the carrier system.

The processing of melatonin with *ginkgo biloba* and biotin in suitable carrier systems may in addition lead to a prevention or delay of melatonin absorption. The normal human plasma level is not influenced thereby. In addition, a longer-lasting effect of the active ingredients can be achieved.

Stable formulations used in cosmetics, especially in the form of cosmetics solutions, can be obtained by formulation in a carrier system.

In the use of specific formulation systems such as liposomes, nanosomes or solid inclusion carriers such as agarose it is possible to obtain compositions which permit controlled delivery of at least one of the active ingredients, in particular of all the active ingredients.

The compositions of the invention are particularly suitable for pharmaceutical or/and cosmetic applications, for example in hair. The compositions may be in the form of a solution, suspension, emulsion, microemulsion, nanosystem, cream, gel, lotion, spray, foam or ointment or any other form suitable for topical applications. They are normally employed in a packaging or application system selected from tubes, bottles, spray bottles, patches, sponges and textile or plastics carriers and other systems suitable for application in the hair. A particularly preferred packaging system are single-dose ampules which provide a dosage unit for one application. The ampules may be fabricated from various materials, e.g. from glass or plastics. Plastics ampules are particularly preferred because plastics ampules ensure safe and satisfactory handling.

Besides the active ingredients, the compositions of the invention may comprise one or more cosmetic or/and pharmaceutical excipients or additives, for example thickeners, minerals, oils, vitamins, e.g. vitamin A, especially in the form of retinoic acid, or fragrances.

The combination preparations of the invention are recommended in particular for application in the evening and display their effect in particular during the night. With this mode of application, the effect of the composition is particularly strong. The compositions of the invention are particularly suitable for stimulation of the hair follicles and a beneficial influence on hair growth.

The treatment takes place in particular in topical applications suitable for use in the hair, which comprise the appropriate concentrations suitable for the particular purpose of use of the active ingredients.

The composition of the invention can be employed for promoting hair growth, in particular for the prevention or/and treatment of alopecia in men or in women. Particularly preferred indications are male-type androgenic alopecia, female-type androgenic alopecia, male-type diffuse alopecia and female-type diffuse alopecia.

The invention is further illustrated by the following example.

EXAMPLE

Composition of a Formulation of the Invention with the Active Ingredients Melatonin, *ginkgo biloba* and Biotin The composition comprises 0.05% by weight of *ginkgo biloba* dry extract, 0.01% by weight of biotin, 0.0033% by weight of melatonin and further additives, water and ethanol. The pH of the composition is between 3.5 and 4.

The invention claimed is:

1. A method of promoting hair growth on a subject in need of such promotion comprising applying to areas of the subject where hair growth is desired a composition comprising active ingredients and a carrier system, wherein said active ingredients consist of
   (a) melatonin or a derivative thereof selected from the group consisting of 5-methoxytryptamine, 5-methoxytryptophan, 5-methoxytryptophol, 5-methoxyindole-3-acetic acid and 6-hydroxymelatonin, and physiologically acceptable salts, esters and complex compounds thereof,
   (b) *ginkgo biloba* and
   (c) biotin.

2. A method of claim 1, wherein the hair growth is promoted in the prevention and or treatment of alopecia.

3. The method as claimed in claim 2, wherein the subject is a man.

4. The method as claimed in claim 2, wherein the subject is a woman.

5. The method as claimed in claim 1, wherein from 0.001 mg to 10 mg of melatonin are administered per application.

6. The method as claimed in claim 5, wherein from 0.01 mg to 1 mg of melatonin are administered per application.

7. The method according to claim 1, wherein said subject is suffering from androgenic or diffuse alopecia.

8. A method of promoting hair growth on a subject in need of such promotion comprising applying to areas of the subject where hair growth is desired, a composition comprising active ingredients, wherein said active ingredients consist of
   (a) melatonin or a derivative thereof selected from the group consisting of 5-methoxytryptamine, 5-methoxytryptophan, 5-methoxytryptophol, 5-methoxyindole-3-acetic acid and 6-hydroxymelatonin, and physiologically acceptable salts, esters and complex compounds thereof,
   (b) *ginkgo biloba* and
   (c) biotin.

9. A method of promoting hair growth on a subject in need of such promotion comprising applying to areas of the subject where hair growth is desired, a composition comprising
   (a) melatonin or a derivative thereof selected from the group consisting of 5-methoxytryptamine, 5-methoxytryptophan, 5-methoxytryptophol, 5-methoxyindole-3-acetic acid and 6-hydroxymelatonin, and physiologically acceptable salts, esters and complex compounds thereof,
   (b) *ginkgo biloba* and
   (c) biotin,
wherein said *ginkgo biloba* and said biotin are in amounts sufficient to delay the absorption of said melatonin or derivative thereof.

* * * * *